United States Patent [19]

Woods

[11] Patent Number: 5,202,568

[45] Date of Patent: Apr. 13, 1993

[54] DETERMINING THE PRESENCE, POSITION, AND INTEGRITY OF REINFORCING MOUNTING CLIPS BY UTILIZING PHOTOELECTRIC MEANS

[75] Inventor: Larry Woods, Corning, Ohio

[73] Assignee: Central Ohio Plastic Corporation, Johnstown, Ohio

[21] Appl. No.: 753,986

[22] Filed: Sep. 3, 1991

[51] Int. Cl.⁵ ............................................. G01N 21/86
[52] U.S. Cl. ................................. 250/561; 250/223 R; 356/376
[58] Field of Search ................. 250/561, 222.1, 223 R; 356/376

[56] References Cited

U.S. PATENT DOCUMENTS 4,799,268 1/1989 Mclean et al. .................. 250/561
4,929,845 5/1990 Amir et al. ..................... 250/561

Primary Examiner—David C. Nelms
Assistant Examiner—T. Davenport
Attorney, Agent, or Firm—Francis T. Kremblas, Jr.

[57] ABSTRACT

The simultaneous monitoring of possibly uncrimped metal reinforcing clips on the mounting arms of a plastic housing or of a warped housing by photoelectric means and the determination of the presence or absence of the clips by electromagnetic switches in combination provide a significant improvement in the assembly and mounting of housing components to frame members.

10 Claims, 1 Drawing Sheet

U.S. Patent    Apr. 13, 1993    5,202,568
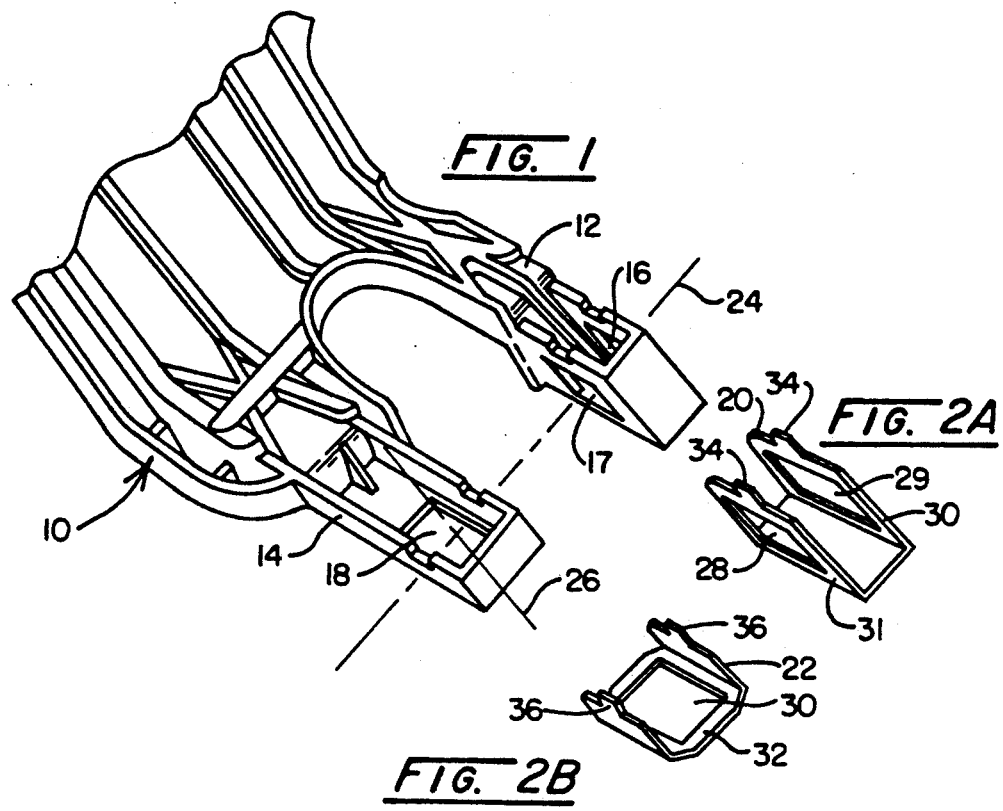
FIG. 1
FIG. 2A
FIG. 2B
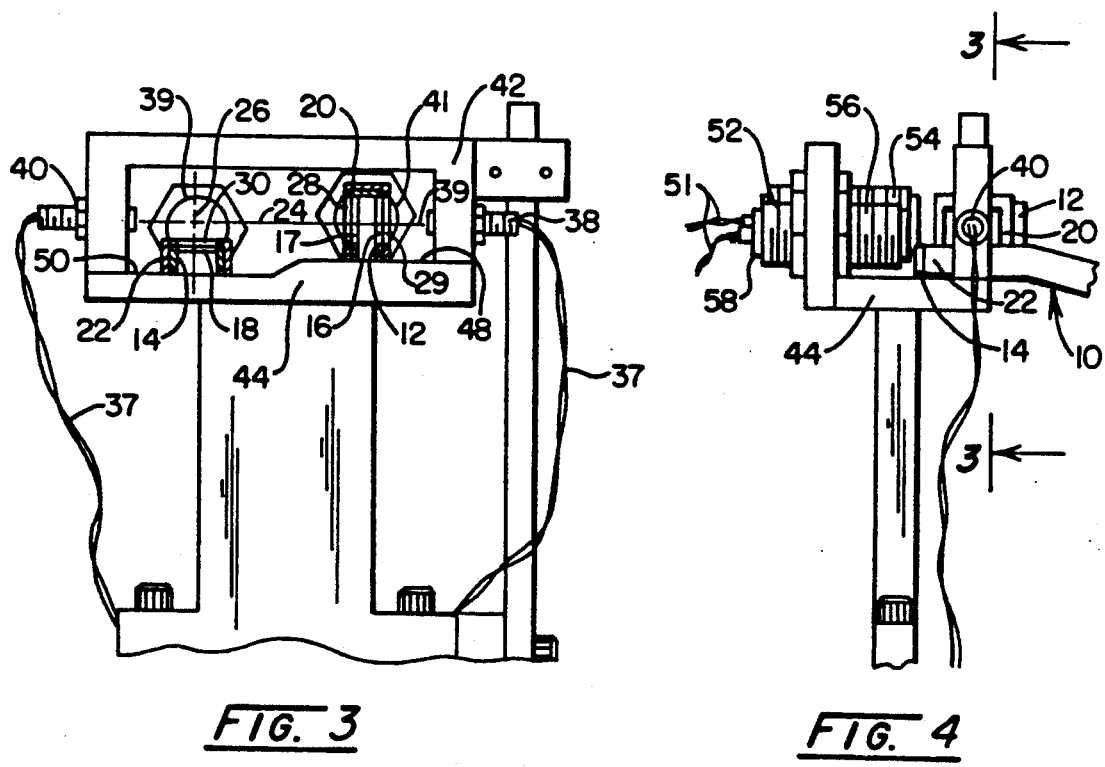
FIG. 3
FIG. 4

DETERMINING THE PRESENCE, POSITION, AND INTEGRITY OF REINFORCING MOUNTING CLIPS BY UTILIZING PHOTOELECTRIC MEANS

TECHNICAL FIELD

The present invention relates generally to inline testing apparatus and methods for confirming defect free assembly of parts.

BACKGROUND ART

The present invention is a method and apparatus for determining the presence, proper positioning and integrity of reinforcing clips for mounting components to vehicles and similar assemblies.

In modern assembly plants, particularly automobile and similar vehicle assembly plants, components such as trim, grills, headlight housings etc. are delivered for mounting on the frame or body of what is being assembled within a few hours of the time such assembly is to take place. Such components are then typically robotically mounted to such frames. As a consequence such components must meet design specifications closely. Small deviations in tolerances or defects in the component can result in down time for the production line or in the production of a defective product.

Component manufacturers and suppliers typically employ varying on-line testing techniques to identify improperly manufactured components and avoid their delivery to an assembly site. However, conventional methods of testing which include visual and mechanical techniques have not assured defect free parts.

SUMMARY OF THE INVENTION

The present invention consists of an improved method and apparatus for determining whether or not metal clips which provide metal reinforcement to fastener openings in plastic parts, such as automobile headlight housings, have been properly seated and attached to the extending mounting arms of such housings. Such clips have extending tabs which must be crimped for proper attachment and the present method determines if such crimping has taken place and additionally whether or not the clips are present. This is accomplished by seating means wherein the mounting arms are positioned on a surface beneath the crimped tabs so that if a tab is not crimped the arm will not seat correctly and will be deflected upwardly. A photoelectric cell or similar device is positioned to determine if such arm is displaced and provide signal means to such distortion, usually indicating an uncrimped tab. An electromagnetic switch simultaneously indicates the presence or absence of such clip or clips.

The invention is useful for housings with two or more arms which can be y tested with a single photoelectric cell (or similar device).

An additional advantage of the tests of the present invention is that they will also detect general distortion in the mounting arms of such housings.

It is the object of the invention to provide testing means to determine if the mounting arms of housings for mounting such housings or to a frame are distorted.

It is also the object of the invention to provide testing means to determine if metal clips that provide fastener perforation to the mounting arms of housings for mounting to frame are present and properly attached.

A further object of the present invention is to provide photoelectric beam and magnetic switch means that will determine the presence or absence and the proper positioning and attachment of metal clips on the mounting arms of an automobile headlight housing.

BRIEF DESCRIPTION OF DRAWINGS

FIG. 1 is a perspective partial view of an automobile headlight housing utilizing metal clip fasteners that are tested in accordance with the process of the present invention.

FIGS. 2A and 2B are perspective views of the metal clip fasteners prior to their incorporation into the automobile headlight housing of FIG. 1.

FIG. 3 is a front view of the testing device positioned as testing the metal clip fasteners as assembled into the housing shown by FIG. 1.

FIG. 4 is a view of FIG. 3 along the line 4—4 snowing the fasteners of FIGS. 1 and 2 being tested.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other elements where such connection is recognized as being equivalent by those skilled in the art.

DETAILED DESCRIPTION

The automobile headlight housing 10 is formed with extending arms 12 and 14 for attachment to the frame or body of an automobile (not shown) by fasteners such as sheet metal screws (not shown) which are projected through openings 16–17 and 18 provided in the end portions of arms 12 and 14 respectively. Openings 16–17 of arm 12 are opposing openings that provide a pathway 24 for the fastener and opening 18 provides pathway 26 for such purpose. Frame 10 is formed of a thermoplastic or soft rubbery plastic such as glass fiber reinforced polyproplyene and consequently openings 16–17 and 18 must be reinforced with metal clips 20 and 22.

Openings 16–17 are disposed to provide a pathway to receive a vertically positioned fastener to attach arm 12 of frame 10 to a projection (not shown) from the automobile frame along the pathway 24 and opening 18 is disposed to receive a horizontally positioned fastener to attach arm 14 of frame 10 to a perforation in the automobile frame (not shown) along pathway 26. U shaped metal clips 20 and 22 are positioned to extend over arms 12 and 14 respectively. Clip 20 is formed with opposing openings 28–29 in the extending arms 30–31 of the clip that correspond to and register with opposing openings 16–17 of arm 12 and provide metal reinforcement for a fastener, such as a sheet metal screw, extended along the pathway line 24. Clip 22 is provided with a opening 33 in the cross member 32 of the clip and metal reinforcement for a fastener such as a sheet screw along pathway 26 of opening 18.

Clips 20 and 22 are each provided with tabs 34 and 36 respectively which project from the extending arms of such U shaped members. In assembly the clips are extended over the arms so that the openings 28–29 of clip 20 registers with openings 16–17 of arm 12 and opening 30 of clip 22 registers with opening 18. Tabs 34 and 36 are crimped to securely lock the clips to the assembly and provide the necessary reinforcement for attachment of arms 12 and 14 to the frame or body of the automobile.

The crimping of tabs 34 and 36 to rigidly attach clips 20 and 22 to the arms 12 and 14 is essential to the satisfactory mounting of the frame 10 to the automobile frame or body.

In spite of consistent manufacturing techniques and rigid inspection it is still possible for assemblies to occur without clips being properly crimped and thus attached to the frame or housing or, in fact, clips may be missing from the housing resulting in unsatisfactorily assembled automobiles. Further, even with properly attached (i.e. crimped) assembly clips the injection molded automobile headlight assembly housing may be distorted in shape particularly in regards to the position of the extending arms 12 and 14 so as to result in an improperly assembled unit.

By use of the present invention it is possible to consistently inspect an assembly such as that shown by FIG. 1 in a manner to assure undistorted headlight assemblies with crimped and positioned clips to automobile assembly lines by means of the process and apparatus of the present invention as depicted by FIGS. 3 and 4.

In the embodiment as shown by FIGS. 3 and 4 photoelectric cell 38 and light source 40 are mounted to a frame 42 that is attached to a suitable table 44 and are positioned to project beam 39 for detection by photoelectric cell 38. Table 44 is provided with and upper level 48 and a lower level 50 positioned so that the extending arms 12 and 14 of the housing 10 which are slightly horizontally displaced may be seated on table 44 and are positioned for testing.

By positioning housing 10 so that the crimped tabs 34 and 36 are adjacent the surfaces 50 and 48 respectively if any of the tabs are not crimped to any extent the respective arm 12 and/or 14 will not seat properly on the table surfaces 50 or 48 and the arm (12 and/or 14) will be higher than intended. Light beam 39 is positioned along a path wherein should one or both of the arm surfaces be too high (off table, surfaces 50 and/or 48) as the result of an uncrimped tab the beam 39 will be interrupted and an appropriate signal will inform the inspector that the clip and housing is defective (i.e. a clip is not crimped) and should are rejected. Such photoelectric units and signal devices are well known commercially available equipment well known to those skilled in testing.

In the embodiment of FIGS. 3 and 4 beam 39 projects along the pathway 24 of the perforations 16-17 of arm 12 and above clip 22 of arm 14 so that if any of the tabs 34 and 36 are not crimped the respective arm 12 and/or 14 will be deflected upwardly and beam 39 will be interrupted by the surface of arm 12 below perforations 16-17 or the top portion of arm 14.

The photoelectric unit arrangement as depicted by FIGS. 3 and 4 will not, of course, detect the complete absence of a clip 20 or 22 which also can occur. This possibility is obviated by using magnetically sensitive metals for clips 20 and 22 such as mild steel and two metal proximity switches 52 and 54 adjacent surfaces 48 and 50. Switches 52 and 54 are essentially electric current carrying coils of wire that generate a magnetic field or flux in the area of a clip. Should a clip be absent from either arm 12 or 14 the effect on the magnetic field or flux is detected by the current flow in switch 52 and/or switch 54 and an appropriate signal will indicate a missing clip. Such metal proximity switches are well known commercially available devices well known to those skilled n the art.

Monitoring beams such as beam 39 of the present description are generated by conventional photoelectric beam detection devices, however such beams may be any detectable beam such as laser light, electron beams or ion beams which may be appropriately interrupted by mispositioned arms such as arms 12 and 14 and which may be used in conjunction with known beam detection devices. Consequently the term used herein to encompass all such beams is "signal beam" and the means for signalling the interruption of such signal beam is referred to as "signal means."

In the practice of the present invention as depicted by FIGS. 3 and 4 an Iritronic PME-7 photoelectric beam device was employed which consists of a beam transmitter (40) and a beam receiver (38). The metal detection proximity switches 52 were Allen Bradly Incuctive Detector #4.13 (x2).

While certain preferred embodiments of the present invention have been disclosed in detail, it is to be understood that various modifications may be adopted without departing from the spirit of the invention or scope of the following claims.

I claim:

1. A method for testing the proper positioning of metal clips that reinforce fastener perforations on the extending mounting arms of plastic components to be attached to a frame member during subsequent assembly comprising:
    a) positioning said arms so that said perforations and clips are positioned on a flat surfaces consistent with the desired position of said arms and clips;
    b) projecting a signal beam juxtaposition said arms with signal means so as to signal any interruption of such beam and indicate any distortion of such arm.

2. The method of claim 1 wherein said clips are formed with projecting tabs which are crimped when said clips are attached to said arms and said arms and clips are positioned on said surface so that if the tabs are not crimped they contact said surface to cause said arm to be deflected upwardly and interrupt said beam.

3. The method of claim 2 wherein there are two arms and two flat surfaces, each arm having separate clips and tabs, such beam being disposed to be interrupted when at least one of said tabs is not crimped so as to distort the position of at least one of said arms.

4. The method of claim 3 wherein said surfaces are at different horizontal levels.

5. The method of claim 4 wherein said housing is an automobile headlight housing.

6. The method of claim 1 wherein electromagnetic proximity switches are positioned adjacent such surfaces disposed to provide a signal to indicate the presence of said clips during such testing.

7. The method of claim 5 wherein electromagnetic proximity switches are positioned adjacent such surfaces disposed to provide a signal to indicate the presence of said clips during such testing.

8. Apparatus for testing the presence and proper positioning of metal clips that reinforce the fastener perforations on the extending mounting arms of plastic components to be attached to frame members comprising:
    a) flat surfaces disposed receive said arms and clips at their desired position:
    b) means for projecting a signal beam over said arms positioned so that said beam will be interrupted if said arms and clips are not properly positioned on said surfaces:

c) signal means disposed to indicate that said signal beam has been interrupted.

9. Apparatus of claim 8 wherein there are two such surfaces positioned at separate horizontal levels to receive two arms and said signal beam means is positioned to project a beam over both said surfaces to detect deflection in at least one of said arms.

10. Apparatus of claim 8 wherein magnetic means is positioned to detect the presence of said clips.

* * * * *